US006901292B2

(12) United States Patent
Hrdlicka et al.

(10) Patent No.: US 6,901,292 B2
(45) Date of Patent: May 31, 2005

(54) CONTROL OF EXTERNALLY INDUCED CURRENT IN AN IMPLANTABLE PULSE GENERATOR

(75) Inventors: Gregory Anthony Hrdlicka, Plymouth, MN (US); Scott Grabinger, Maple Grove, MN (US); Marc Stein, Chandler, AZ (US); Dave Mueller, Roseville, MN (US); Wilbert Wesselink, Viatron (NL)

(73) Assignee: Medtronic, Inc., Minneapolis, MN (US)

( * ) Notice: Subject to any disclaimer, the term of this patent is extended or adjusted under 35 U.S.C. 154(b) by 164 days.

(21) Appl. No.: 10/034,945

(22) Filed: Dec. 27, 2001

(65) Prior Publication Data

US 2002/0133204 A1 Sep. 19, 2002

Related U.S. Application Data

(60) Provisional application No. 60/277,076, filed on Mar. 19, 2001.

(51) Int. Cl.⁷ .............................................. A61N 1/375
(52) U.S. Cl. ............................... 607/27; 607/9; 607/36; 607/63
(58) Field of Search ................................ 607/9, 36, 63, 607/64, 27, 37, 38; 128/908

(56) References Cited

U.S. PATENT DOCUMENTS

| 3,678,937 A | * | 7/1972 | Cole et al. ..................... 607/9 |
| 3,915,174 A | | 10/1975 | Preston |
| 4,038,990 A | | 8/1977 | Thompson |
| 4,220,813 A | | 9/1980 | Kyle |
| 4,320,763 A | | 3/1982 | Money |
| 4,726,379 A | | 2/1988 | Altman et al. |
| 4,991,583 A | | 2/1991 | Silvian |
| 5,018,523 A | | 5/1991 | Bach, Jr. et al. |
| 5,197,468 A | | 3/1993 | Proctor et al. |
| 5,217,010 A | | 6/1993 | Tsitlik et al. |
| 5,476,496 A | | 12/1995 | Strandberg et al. |
| 5,683,435 A | | 11/1997 | Truex et al. |
| 5,751,539 A | | 5/1998 | Stevenson et al. |
| 5,814,076 A | | 9/1998 | Brownlee |
| 5,905,627 A | | 5/1999 | Brendel et al. |
| 6,198,972 B1 | * | 3/2001 | Hartlaub et al. .............. 607/63 |

FOREIGN PATENT DOCUMENTS

| EP | 0713714 A2 | 5/1996 |
| WO | WO 97/41923 A1 | 11/1997 |

* cited by examiner

Primary Examiner—Angela D. Sykes
Assistant Examiner—Roderick Bradford
(74) Attorney, Agent, or Firm—Banner & Witcoff, Ltd.

(57) ABSTRACT

The present invention takes the form of a current limiting apparatus and method for limiting current flow, induced when the level of an external signal is greater than an external signal threshold signal level, in a conductive loop formed by a medical device implanted within a living organism having electrically excitable tissue. The system includes an implantable pulse generator (IPG) system having a housing, a signal generator disposed in the housing that generates an electrical signal, and at least one lead extending from the housing to convey electrical signal to the patient. To limit the induced current flow, the IPG includes current limiting componentry, an impedance increasing element, and/or alternating current blocking elements. These components provide an alternating current impedance path to the electrical ground from a lead coupled to the capacitive element. Also disclosed are techniques for reducing the effective surface area of the current inducing loop caused by the IPG system.

24 Claims, 9 Drawing Sheets

FIG. 1
(PRIOR ART)
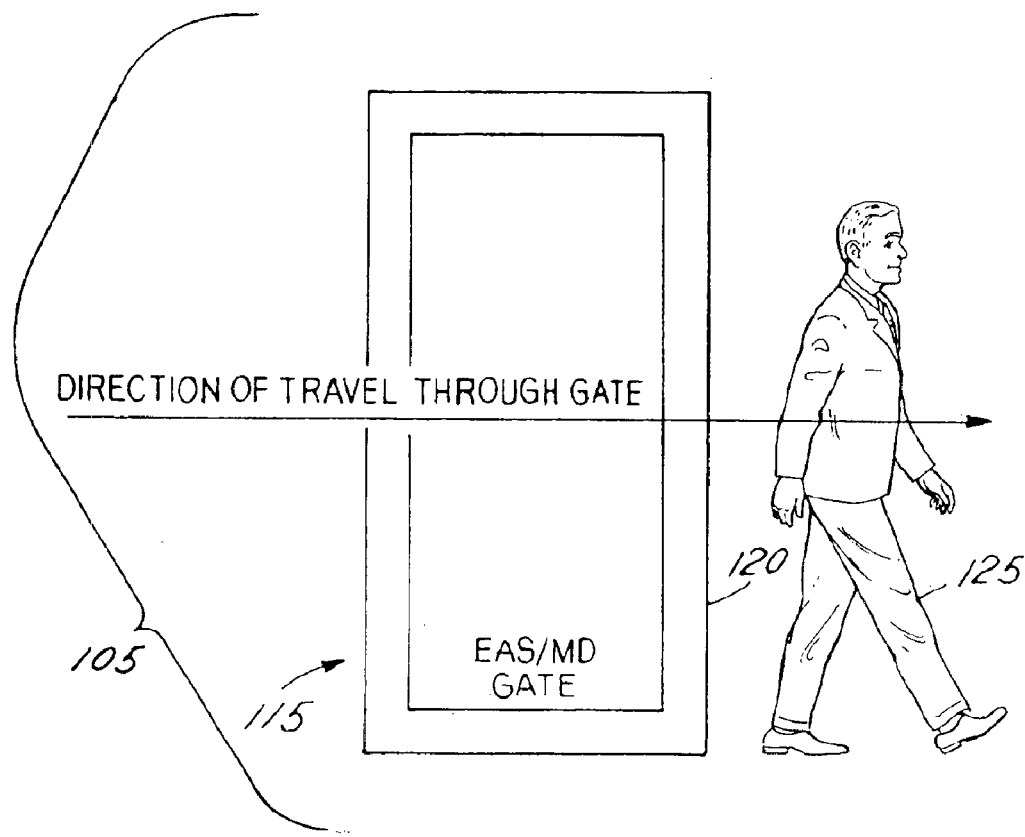
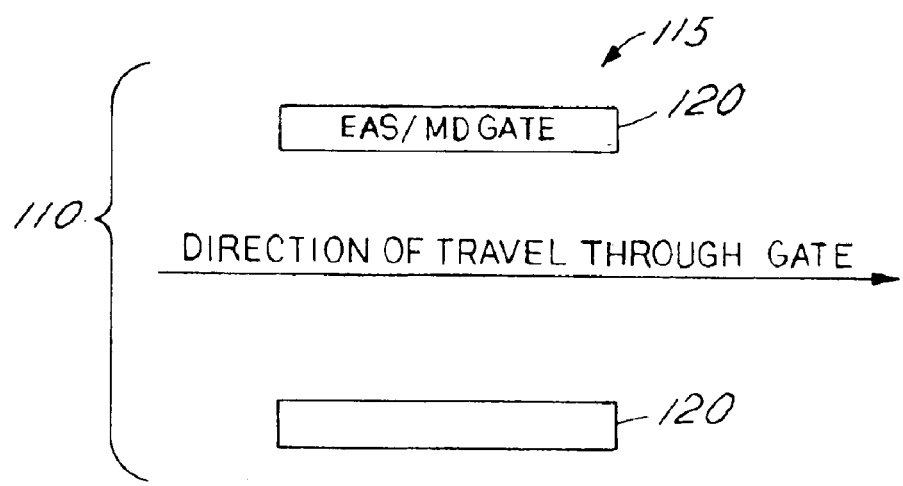

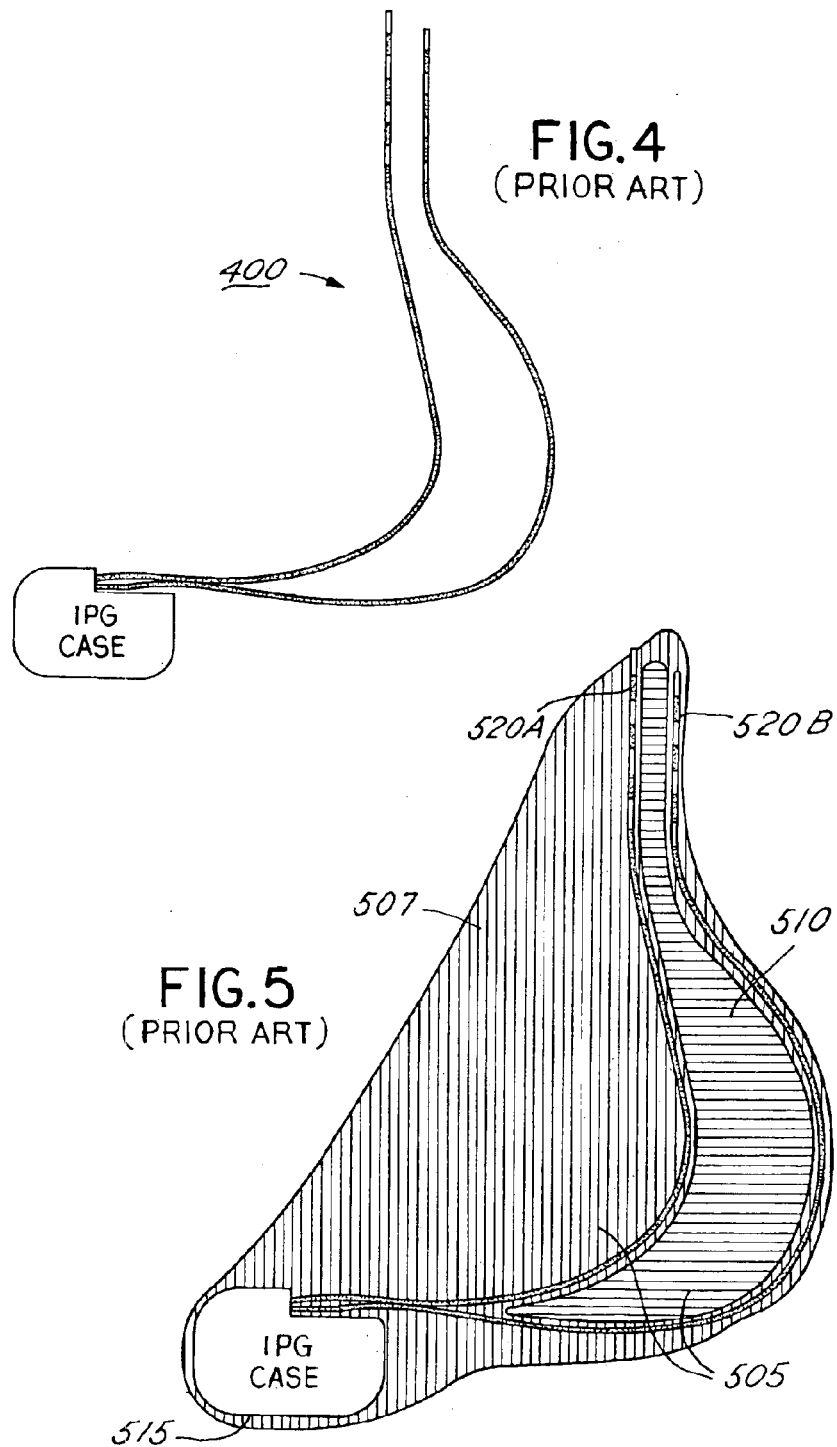

C1 thru Cn =
Feedthrough Capacitors
(part of feedthrough or separate capacitors)

Cn+1 = common EMC capacitor to IPG case

Z1 thru Zm =
Impedance elements on outboard side of feedthroughs
(may be ferrite bead, resistor, or inductor)

S1 = case electrode switch (may be electronic or mechanical such as a reed switch)

FIG.7

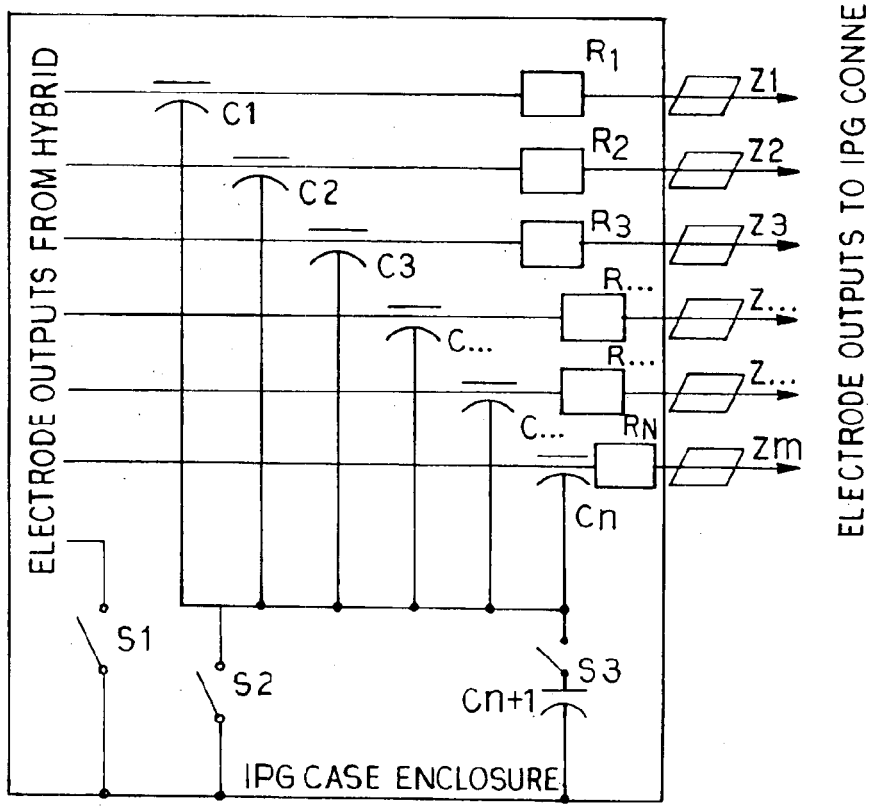

$C_1$ thru $C_n$ =
Feedthrough Capacitors
(part of feedthrough or separate capacitors)

$C_{n+1}$ = single case electrode $Z_1$ thru $Z_m$ = AC current blocking element.
Impedance elements on outboard side of feedthroughs capacitors
(may be ferrite bead, resistor, or inductor)

$S_1$ = optional switching device $S_2$ = optional switching device $S_3$ = optional switching device $R_1 - R_N$ = optional resistors

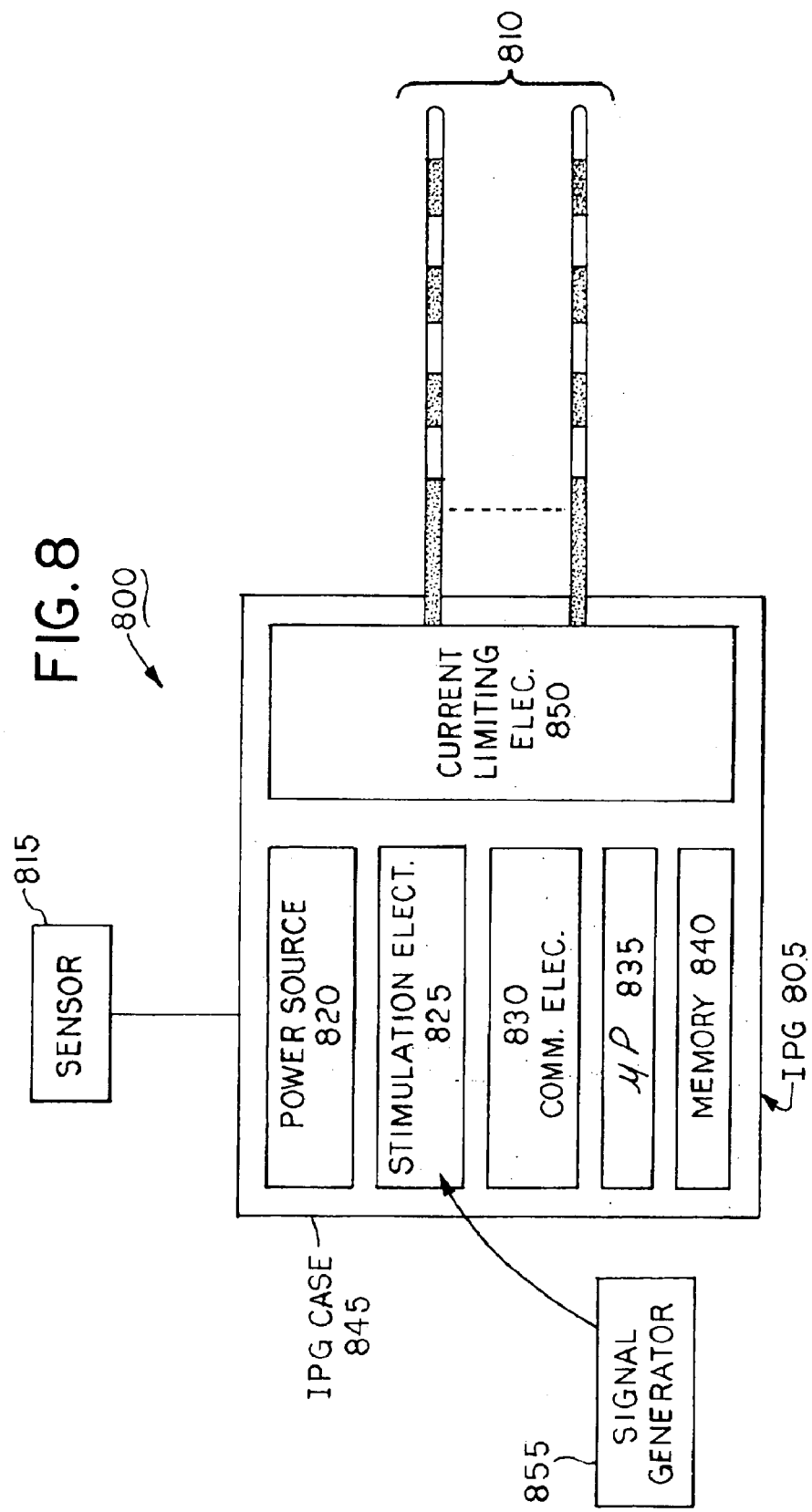

FIG. 9
REGULAR BIPOLE
(6.5 mm SPACING)
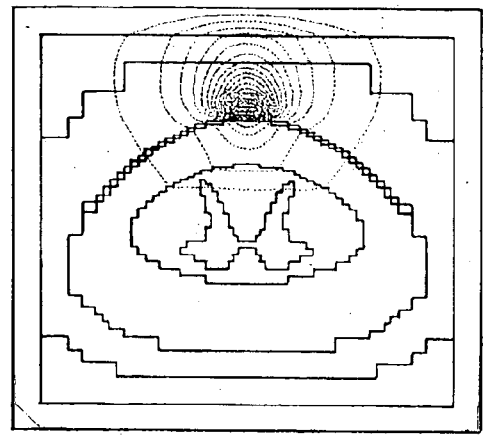
VIRTUAL MONOPOLE
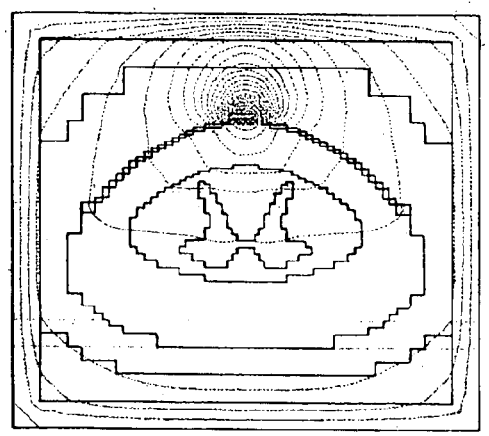
MONOPOLE
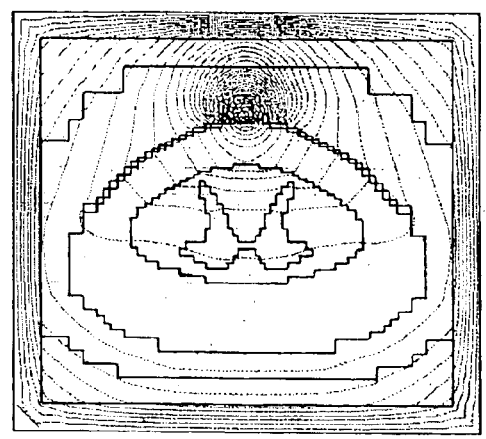

FIG.10
REGULAR BIPOLE 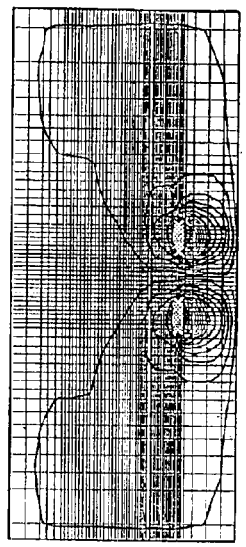 VIRTUAL MONOPOLE 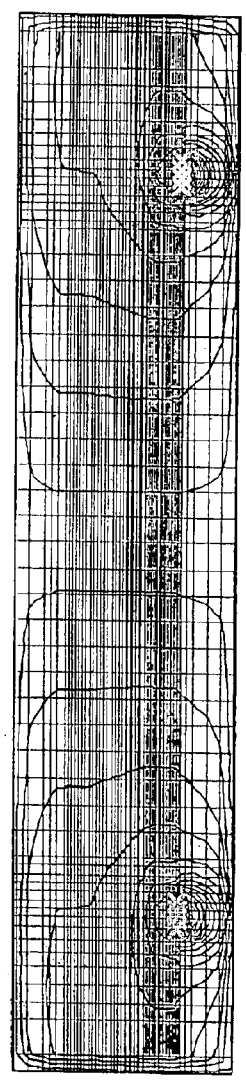 MONOPOLE 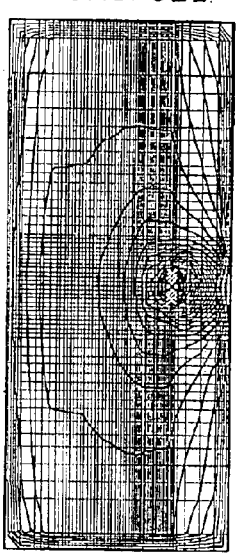

FIG. 11
REGULAR BIPOLE
(6.5mm SPACING)
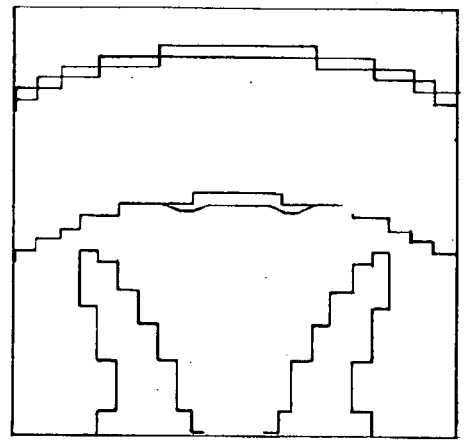
VIRTUAL MONOPOLE
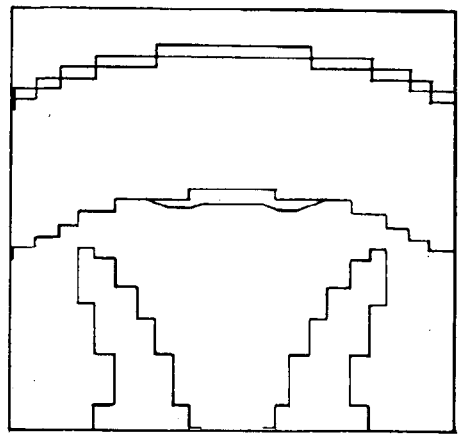
MONOPOLE
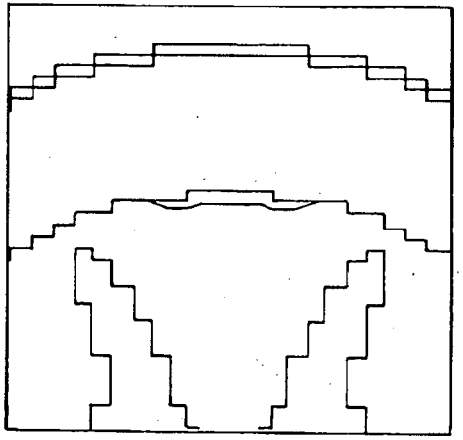

CONTROL OF EXTERNALLY INDUCED CURRENT IN AN IMPLANTABLE PULSE GENERATOR

This application claims priority to provisional U.S. Application Ser. No. 60/277,076, filed Mar. 19, 2001.

FIELD OF THE INVENTION

The invention relates generally to implantable medical devices, and more particularly to a method and apparatus for limiting unwanted current flow through electrically excitable tissue resulting from application of an external signal on an implanted medical device.

BACKGROUND OF THE INVENTION

The use of implantable medical devices for electrical stimulation of electrically excitable tissue is well known in the medical arts. For example, electrical stimulation of the brain, the spinal cord, or a peripheral nerve may be used to treat any number of medical conditions. In such devices, electrodes deliver the stimulation of signal to the electrically excitable tissue. The electrodes are operatively connected to an implantable pulse generator (IPG) that is packaged in a case that is adapted to be implantable. Those electrodes are coupled to that pulse generator by a conductive lead wire.

A user having such an implantable medical device during normal life activities may be forced to go through a time-alternating electromagnetic field. Prevalent examples of sources of electromagnetic field are Electronic Article Surveillance (EAS) systems and Metal Detectors (MD). Such systems detect theft of articles that have an attached electromagnetic tag and are found in the exit doorways of many stores and libraries.

EAS/MD systems work by generating an electromagnetic field that retail customers must pass through at the entrance and/or exit from a business establishment or other protected area. EAS systems detect the presence of antitheft tags on merchandise as they pass through the electromagnetic field if they have not been deactivated. Similarly, metal detectors (MD) generate an electromagnetic field that is perturbed by the presence of metal objects that might be carried by a person passing through the metal detector. Both these systems can induce voltages, via Faradays Law, on the lead system of implantable stimulators. The induced voltage is proportional to the area formed from one end of the lead to the other end of the lead (e.g. from the IPG case to the end of the lead). More specifically, according to Faraday's law, the voltage induced on a wire (lead system) is proportional to: (A) the area X number of turns described by the wire; (B) the flux density of the electromagnetic field; C) the frequency of the magnetic field; and (D) the cosine of the angle between the electromagnetic field and the vector normal to the area described by the wire. For dual lead systems, an induced voltage may also appear across the distal ends of the leads and is proportional to the area formed between the two leads.

These induced voltages may be of sufficient voltage and pulse duration to cause undesired tissue stimulation in the patient. This may result in shocking sensations to the patient, pacing of the heart, IPG sensing irregularities or other undesired stimulation effects. Additionally, in some medical devices with sensing, the induced voltage may also cause a false "sensing" response.

One technique for minimizing the effects of induced voltages is to keep the lead length of the implanted system to a minimum and/or to keep the lead in a straight line to minimize the loop area generated by the lead system. However, it may not always be possible to minimize the loop area or lead length. Another technique for minimizing the effects of induced voltages is to restrict the IPG to bipolar use only since this disconnects the case from the lead. However, this is not entirely effective since the electronic switch to the case may become forward biased (conductive) if the induced voltage is sufficiently high. Another problem with this approach is that it requires feedthrough capacitors on each of the IPG outputs to reduce the susceptibility to high frequency RF. Feedthrough capacitors can act as a low impedance connection between the lead and the IPG case at EAS/MD frequencies, thereby negating the benefit of bipolar stimulation. See U.S. Pat. Nos. 5,751,539 and 5,905,627.

It is therefore desirable to provide a way to improve electromagnetic compatibility (EMC) with EAS/MD systems that overcomes the disadvantages of the prior art. Moreover, it is desirable to improve EMC with EAS/MD systems while still allowing the use of unipolar stimulation.

BRIEF SUMMARY OF THE INVENTION

The present invention takes the form of a current limiting apparatus and method for limiting current flow, induced when the level of an external signal is greater than an external signal threshold signal level, in a conductive loop formed by a medical device implanted within a living organism having electrically excitable tissue. The present invention includes an implantable pulse generator (IPG) system having a housing, a signal generator disposed in the housing that generates an electrical signal, and at least one lead extending from the housing to convey electrical signal to the patient. To limit the induced current flow in accordance with a first embodiment, the IPG includes current limiting componentry having a capacitive element electrically coupled to each lead and an impedance increasing element serially coupled between each of the capacitive elements and an electrical circuit path (e.g., an electrical ground). The capacitive element together with the impedance increasing element provide an alternating current impedance path to the electrical ground from a lead coupled to the capacitive element.

Optionally, the IPG may further include a first switching device coupled between the capacitive element and the electrical ground, a second switching device coupled between the capacitive element and the impedance increasing element, and a signal sensor for sensing an external signal. The signal sensor is coupled to the first and second switching devices and disables the first switching device and enables the second switching device when the sensor senses that a level of the external signal is greater than an external signal threshold.

In another embodiment, the IPG system includes current limiting componentry having a capacitive element electrically coupled to each lead and an alternating current blocking element coupled between each capacitive element and the associate lead. The alternating current blocking element include, for example and without limitation, a ferrite bead, a resistor, and/or an inductor.

In yet another embodiment, the IPG includes a switching device disposed in the housing and coupled to an electrical ground and includes an external signal sensor for sensing an external signal. Activation and deactivation of the switching device causes the medical device to switch between a unipolar mode of operation and a bipolar mode of operation. The external signal sensor is coupled to the switching device and causes the switching device to convert the medical device from a unipolar mode of operation to a bipolar mode of operation when the sensor senses that a level of the external signal is greater than an external signal threshold.

In still another embodiment, the IPG system may operate in a distal unipolar mode to reduce the effective surface area from which unwanted current is induced. The IPG system may include a plurality of leads where each at least one lead is in electrical communication with the signal generator and conveys the electrical signal to the patient and where at least one other lead is coupled to a electrical ground.

In even enother embodiment, the IPG system may operate in a virtual unipolar mode to reduce the effective surface area from which unwanted current is induced. The IPG system may include a lead having a plurality of electrical conductors that each extend from a proximal section of the lead to a distal section of the lead. At least one of the electrical conductor of the lead may be coupled to the signal generator and at least one other electrical conductor of the lead may be coupled to a electrical ground.

These techniques of the present invention improve IPG EMC compatibility with other electrically noisy environments that may be problematical to patients implanted with neurostimulators. Such environments may be, for example, industrial manufacturing sites with high power electrical machinery, power line substations, or home environments with certain types of appliances such as induction cookstoves or amateur radio transmitters.

These and other features and advantages of the present invention will be better understood by considering the following detailed description of the invention which is presented with the attached drawings.

BRIEF DESCRIPTION OF THE DRAWINGS

FIG. 1 illustrates a side view and a top view of a typical EAS/MD installation.

FIG. 4 illustrates another variation of the IPG system having a dual (multiple) lead system.

FIG. 5 illustrates the loop areas formed from the ends of the leads to the case of the IPG of FIG. 4.

FIG. 7 illustrates another preferred embodiment of the current limiting electronics.

FIG. 8 illustrates a schematic block diagram of an IPG system in accordance with a preferred embodiment of the present invention.

FIG. 9 shows the potential fields in a transverse section of the various models at the height of the cathode.

FIG. 10 shows sagittal sections of the same models of FIG. 9 at the height of the contacts.

FIG. 11 shows recruitment zones.

DETAILED DESCRIPTION OF THE INVENTION

Figure 2:
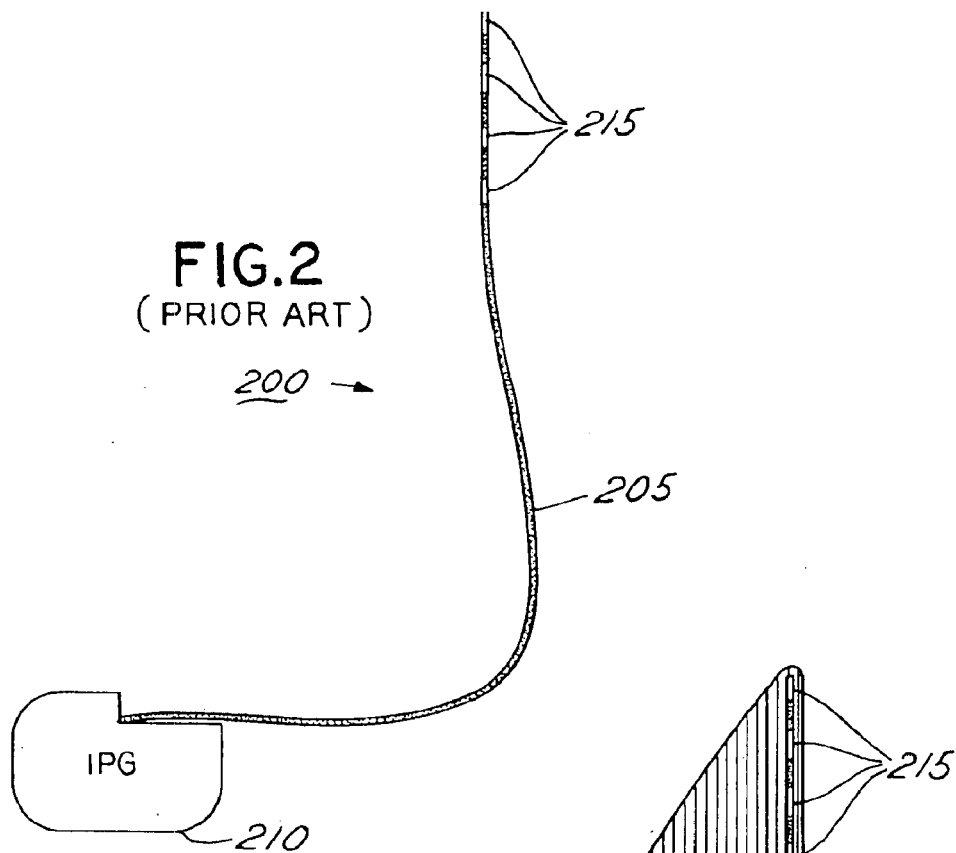
FIG. 2 illustrates a typical single lead implantable pulse generator (IPG) system.

As exemplified herein, the invention may be embodied in various forms. The present invention is generally a current limiting apparatus and method for limiting current flow, induced when the level of a signal is greater than an external signal threshold signal level, in a conductive loop formed by a medical device implanted within a living organism having electrically excitable tissue.

FIG. 1 illustrates a side view 105 and a top view 110 of a typical installation of an Electronic Article Surveillance (EAS) or Metal Detector (MD) installation 115. Most systems consist of one or more panels 120 located across the entrance and/or exits of the retail businesses or other areas to be protected. As a person 125 passes between the gates, they are subjected to an electromagnetic field that is used to sense the presence of "activated" theft detector tags or the presence of metal objects. If activated tags or metal are detected, an alarm will be generated. MD and EAS systems may also include handheld devices.

The characteristics of the electromagnetic field vary between manufacturers and different model detectors but, in general, they produce a time varying electromagnetic field from a few hundred hertz to tens of megahertz in frequency. These electromagnetic fields may induce a voltage onto the lead system of implanted medical devices via an effect known as Faraday's law (discussed above). The embodiments of the present invention illustrate several techniques that can be used to minimize the effects from induced voltages on lead systems for Implantable Pulse Generators (IPGs), especially those effects that result in direct tissue stimulation.

FIG. 2 illustrates a typical single lead IPG system 200. The IPG system 200 includes a lead 205 coupled to an IPG 210 at one end and to one or more electrodes 215 at the other end. Optionally, the IPG system 200 may include one or more sensors to provide closed-loop feedback of the treatment therapy. As is typical of such IPG systems, the lead 205 follows the contour of the human body and therefore creates a loop that is susceptible to induced voltages.

Figure 3:
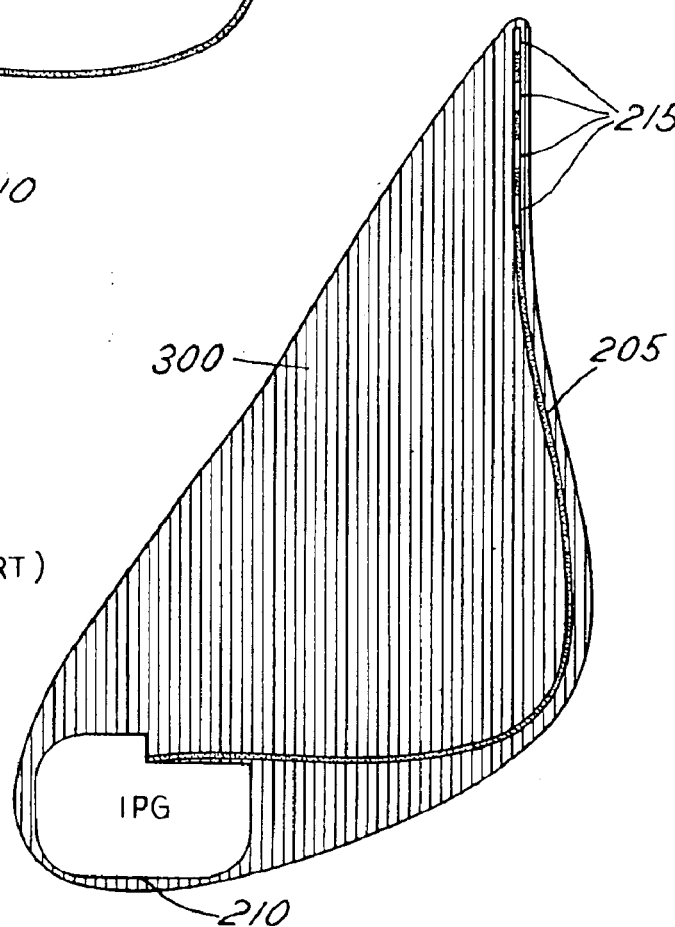
FIG. 3 illustrates the loop area formed from the end of the lead to the case of the IPG of FIG. 2.

For example, FIG. 3 illustrates the loop area 300 (vertical line fill area) formed from the electrode end of the lead 205 to the case of the IPG 210. With all other variables equal, the greater the loop area 300, the greater the induced voltage. Other variations of this may further contribute to increased magnitude of induced voltages. For example, excess lead length could be looped several times around the IPG 210, thus creating even greater loop area.

Another variation of the IPG system 200 is a dual (multiple) lead system 400 shown in FIG. 4. Here, three loop areas 505, 507 and 510 are formed that may lead to induced voltages as illustrated in FIG. 5. One loop area 505 is formed from the area defined by the IPG case 515 and the lead 520B (vertical line fill area including horizontal line fill area).,A second loop area 507 is formed by the area defined by the IPG case 515 and the lead 520A (vertical line fill area excluding horizontal line fill area). A third loop area 510 is formed by the area defined by the two leads 520A–B (horizontal line fill area). Each of the loop areas 505, 507 and 510, either separately or together, can result in tissue stimulation via induced voltages or sensing irregularities. In the first case, tissue stimulation occurs from current flowing out the end of the lead 520A, through the tissue, into the IPG case 515, and then through the lead 520A. In the second case, tissue stimulation can occur from current flowing out one lead 520A, through the tissue, into the other lead 520B, through the IPG , and back out from the original lead 520A. In the third case, tissue stimulation occurs from current flowing out the end of the lead 520B, through the tissue, into the IPG case 515, and then through the lead 520B. The above embodiments of FIGS. 2–5 serve to illustrate two common IPG 210, 510 implant situations. Those skilled in the art will appreciate that other variations may also occur such as an IPG system with three or more leads, some of which may go to different parts of the body.

In accordance with a general preferred embodiment of the present invention, FIG. 8 illustrates a schematic block diagram of an IPG system 800. The IPG system 800 generally includes an IPG 805 and one or more leads 810. Leads 810 extend from the IPG 805, are in electrical communication with a signal generator within the IPG 805, and convey electrical signal energy to electrically sensitive tissue of the patient. Optionally, the system 800 may include one or more sensors 815 to sense an external signal that may be greater than an external signal threshold. The IPG 805 has an IPG case or housing 845 and generally contains therein a power source 820, stimulation electronics 825 (including a signal generator that generates an electrical signal), communication electronics 830, a microprocessor 835, and a memory 840. IPGs are generally well understood and those skilled in the art will appreciate that any number of IPG configurations may be implemented and still be considered within the scope of the present invention. Also included in the IPG 805 is current limiting electronics 850, which is described in further detail herein.

Figure 6:
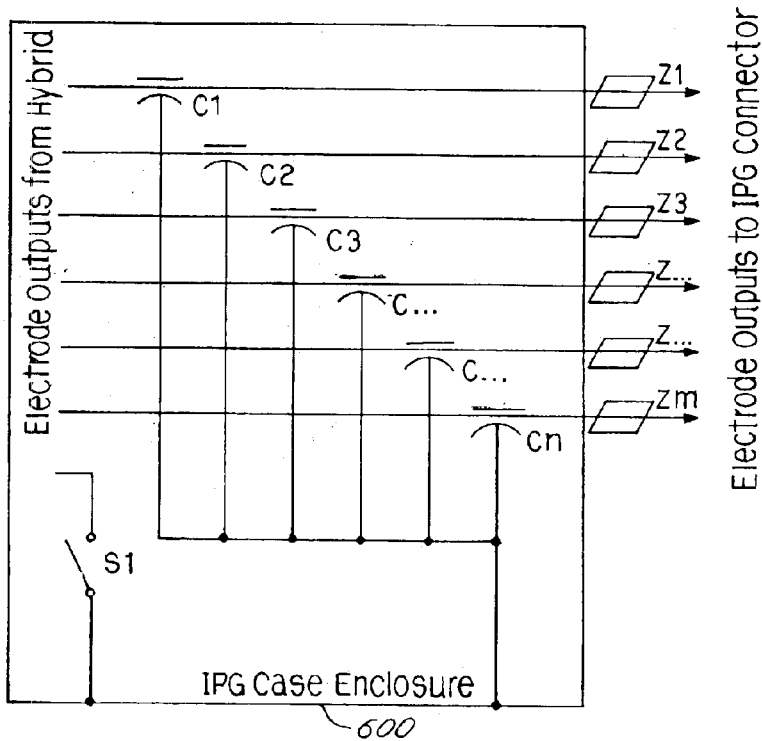
FIG. 6 illustrates one preferred embodiment of the current limiting electronics.

FIG. 6, which illustrates one preferred embodiment of the current limiting electronics 850, shows an IPG case enclosure 600 for a single lead IPG and having current limiting componentry comprising at least one capacitive element electrically coupled to at least one lead. In the example of FIG. 6, the capacitive elements are feedthrough capacitors, C1 through Cn, coupled to each output of the IPG case. Also included are alternating current blocking elements (Z1–Zm) coupled between the capacitive elements and a distal end of the lead. The alternating current blocking element may include, for example and without limitation, an inductive element, a ferrite bead, a resistor, an electrical switch and/or other electrical componentry to provide current-limiting effect. Optionally, the current limiting electronics 850 may include at least one resistor and/or other current limiting componenty coupled between the capacitive element and a distal end of the lead.

Switch S1 is a switch that may be closed to connect the IPG output to the case for unipolar stimulation or if left open, to set the IPG to bipolar stimulation. EAS/MD susceptibility is worst if switch S1 is closed (unipolar stimulation) as the induced voltage on the lead system allows current to flow out the end of the lead, through the tissue, through the IPG can, and back into the lead. Switch S1 is coupled to an electrical circuit path (e.g., an electrical ground) such that activation and deactivation of the switching device causes the medical device to switch between a unipolar mode of operation and a bipolar mode of operation. A signal sensor may optionally be used for sensing an external signal that is proportional to the EAS/MD electromagnetic field. The signal sensor may be coupled to switch S1 to cause switch S1 to convert the medical device from a unipolar mode of operation to a bipolar mode of operation when the sensor senses that a level of the external signal is greater than an external signal threshold.

Capacitors C1 through Cn may be individual capacitors located in the IPG or integrated into the IPG feedthrough. This is known EMC control technique and the capacitors are commonly used in commercially available IPGs to improve electromagnetic compatibility (EMC) by shorting radio frequency (RF) signals on the lead system to the IPG case. This helps to keep RF signals away from the electronics in the IPG and thereby minimize EMC susceptibility. However, each of these capacitors can present sufficiently low impedances from the lead to the case at EAS/MD frequencies to cause undesired tissue stimulation or sensing irregularities, even if the case switch S1 is open (bipolar stimulation).

In accordance with one embodiment of the present invention, impedance elements Z1 through Zm may be used instead of or in addition to capacitors C1 through Cn. The impedance elements, especially for higher RF frequencies, may be used to minimize EMC susceptibility. They may be ferrite material or beads, inductors, or resistors that may be used to improve EMC compatibility at higher RF frequencies. No known IPG's currently use these impedance elements (Z1 . . . Zm) for EMC control.

FIG. 7, which illustrates another preferred embodiment of the current limiting electronics 850, shows how IPG EAS/MD compatibility can be improved by adding at least one impedance increasing element (in this example, one additional capacitor, Cn+1) between the common point of the feedthrough capacitors and the case, in accordance with another embodiment of the present invention. Capacitor Cn+1 is serially coupled between the capacitive elements (C1–Cn) and an electrical circuit path (e.g., an electrical ground), wherein the capacitive elements together with the impedance increasing element provides an alternating current impedance path to the electrical ground from a lead coupled to the capacitive element.

If switch S1 is open (bipolar stimulation), capacitor Cn+1 in this configuration reduces the capacitance between the lead and the IPG case. This substantially increases the impedance to the case and thereby reduces current flow from the EAS/MD induced voltage on the lead system. If switch S1 is closed (unipolar stimulation), this improvement is no longer effective. However, if a sensing circuit is provided to detect the presence of EAS/MD signals and immediately open switch S1, then capacitor Cn+1 is again effective in reducing current flow from induced voltages on the lead system. The sense circuit may be implemented by looking for any EAS/MD induced voltages or currents on the lead system that are greater than the programmed EAS/MD voltage or current threshold level and then opening switch S1. Alternatively, the telemetry antenna or other coil/transformer may be used to sense the EAS/MD electromagnetic field and again open switch S1. The sensing circuit may sense an EAS/MD magnetic field, for example, by way of a Hall effect or other magnetic field sensor. Still another method is to place a switch (electrical or mechanical) in series with the case connection that the patient can open at will, either by programming or the use of a magnet, while passing through the EAS/MD gates.

The above embodiments of the current limiting electronics 850 may also include first switching devices coupled between each capacitive element and electrical ground and second switching device coupled between each capacitive element and the impedance increasing element. A signal sensor may thereby be implemented for sensing an external signal. The signal sensor may be coupled to the switching devices to disable the first switching devices and enable the second switching devices when the sensor senses that a level of the external signal is greater than an external signal threshold.

From the above discussion, a bipolar configuration is better at improving EAS/MD compatibility, however, some therapies are better served by unipolar stimulation. These conflicting requirements can be satisfied by insulating the case and moving the indifferent (unipolar) electrode from the IPG case to an area nearer to the distal end of the lead, thereby reducing the effective loop area. This can be done by removing the unipolar output connection from the IPG can and then moving it to the IPG connector. From the IPG connector, it is then run to an indifferent electrode that is implanted near the distal end of the lead. An improvement to this concept is to eliminate the additional indifferent electrode and then use the unused (open) electrodes on the lead as anodes. According to electric field modeling done by Dr. Holsheimer and Mike Schendel, electrodes that are more than several millimeters from a cathode behave like a unipolar electrode. Therefore, electrodes that would normally be programmed open on a lead can be used as a "Virtual" unipolar electrode if they are programmed positive. This also eliminates the need for a separate indifferent electrode output. For this concept to work, the IPG case needs to be electrically insulated between the hybrid/lead assembly and the body tissue to prevent current flow through the IPG case. This can be accomplished by coating the entire IPG can with an insulator such as Parylene. Alternatively, the IPG can remain uncoated but not connected to the hybrid/lead. If filtered feedthroughs are needed for EMC control, then the additional capacitor Cn+1 of FIG. 7 may be used to minimize current flow from EAS/MD induced voltages on the lead system.

Computer modeling of spinal cord stimulation (SCS) with the UT-SCS model has been applied for many years to gain understanding of the mechanisms underlying SCS. This model allows analysis of potential fields, current density fields and fiber recruitment in the spinal cord due to stimulation with various contact configurations. To improve the EAS/MD compatibility, the effective loop area can be lowered by having an indifferent electrode configuration, i.e. instead of the can of IPG being the indifferent electrode the indifferent electrode is placed nearer to the distal end of the lead.

The computer modeling results show that the effects true monopole and virtual monopole are similar. Having an indifferent electrode nearer to the distal end of the lead (instead of the IPG case) is similar to having a true monopole.

Computer modeling was performed using the following criterion:
  a. Geometry of volume conductor model: standard mid-cervical, i.e. CSF width=2.4 mm.
  b. Contact geometry: Pisces Quad geometry, i.e. contact width=1 mm and contact height=3 mm. Bipolar configurations with 6.5 and 82 mm edge-to-edge spacing.
  c. Fiber parameters: Medial dorsal column fiber, 10 $\mu$m diameter with collaterals (3.33 $\mu$m) attached. Recruitment zones are calculated at 1.25 times the threshold of the 10 $\mu$m dorsal column fiber.

The results are presented as a comparison of a regular bipolar configuration (6.5 mm spacing), a bipolar configuration with a wide contact spacing of 82 mm (the virtual monopolar configuration) and a true monopolar configuration.

FIG. 9 shows the potential fields in a transverse section of the 3 models at the height of the cathode, whereas FIG. 10 shows sagittal sections of the same models at the height of the contacts. Compared against the monopole and the virtual monopole, the potential field of the regular bipole is much more confined. This is due to the presence of the anode near the cathode. Without an edge effect, the field at the cathode of the virtual monopole would even be more similar to the field of the monopole in the sagittal view.

Recruitment zones are shown in FIG. 11. The recruitment zones of the monopole and the virtual monopole do not differ, whereas the recruitment zone of the regular bipole is less extended dorso-ventrally as well as laterally. This difference would be much more pronounced when comparing against a bipole with much smaller spacing (i.e. 2–3 mm). In view of the these modeling results, the EAS/MD compatibility of IPG systems can be improved by lowering the effective loop area, which can be achieved by having an indifferent electrode configuration. In other words, instead of the IPG case being the indifferent electrode, the indifferent electrode is placed nearer to the distal end of the lead. The indifferent electrode may be those of a lead in a multi-lead IPG system (distal unipolar mode), or may be one or more particular electrodes of multi-electrode, single-lead IPG system (virtual unipolar mode).

Accordingly, in one preferred embodiment of the present invention, the IPG system 800 may operate in a virtual unipolar mode. Lead 810 of IPG system 800 may comprise a plurality of electrical conductors that each extend from a proximal section of the lead 810 to a distal section of the lead 810, wherein a first electrical conductor of the plurality of electrical conductors is coupled to the signal generator 855, and wherein a second electrical conductor of the plurality of electrical conductors is coupled to an electrical ground. When an alternating current is externally induced in the first electrical conductor, a portion of the alternating current is coupled to the electrical ground via the second electrical conductor.

In another preferred embodiment where the IPG system 800 is a multi-lead system, the IPG system 800 may be configured to operate in a distal unipolar mode. The IPS system 800 may include a first set of one or more leads may be in electrical communication with the signal generator 855 and convey the electrical signal to the electrically sensitive tissue of the patient while a second set of one or more leads may be coupled to a electrical ground. Accordingly, when an alternating current is externally induced in the first lead, a portion of the alternating current is coupled to the electrical ground via the second lead.

These techniques of the present invention improve IPG EMC compatibility with other electrically noisy environments that may be problematical to patients implanted with neurostimulators. Such environments may be, for example, industrial manufacturing sites with high power electrical machinery, power line substations, or home environments with certain types of appliances such as induction cookstoves or amateur radio transmitters.

The techniques of the present invention may be implemented within any number of IPG applications including Spinal Cord Simulation (SCS), Deep Brain Stimulation (DBS), Vagal Nerve Stimulation (VNS), pacemaker, Peripheral Nerve Stimulation (PNS), and the like.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

We claim:
1. An implantable pulse generator (IPG) system limiting undesired current flow comprising in combination:
  (a) an IPG housing
  (b) a signal generator disposed in the housing that generates an electrical signal;
  (c) at least one lead extending from the housing and in electrical communication with the signal generator, wherein the lead conveys the electrical signal to electrically sensitive tissue;
  (d) current limiting componentry within the IPG case comprising at least one capacitive element electrically coupled to at least one lead;
  (e) at least one impedance increasing element serially coupled between the capacitive element and an elec- trical ground, wherein the capacitive element together with the impedance increasing element provides an alternating current impedance path to the electrical around from a lead coupled to the capacitive element; and (f) a first switching device coupled between the capacitive element and the electrical ground.

2. The IPG system of claim 1, further comprising:

(g) a signal sensor for sensing an external signal, wherein the signal sensor is coupled to the first switching device and wherein the signal sensor disables the first switching device when the sensor senses that a level of the external signal is greater than an external signal threshold.

3. The IPG system of claim 2, wherein the sensor comprises a telemetry antenna.

4. The IPG system of claim 2, wherein the sensor comprises a coil/transformer.

5. The IPG system of claim 2, wherein the sensor comprises a lead voltage sensor.

6. The IPG system of claim 2, wherein the sensor comprises a lead current sensor.

7. The IPG system of claim 2, wherein the sensor comprises a sensor for sensing a magnetic field effect.

8. The IPG system of claim 3, wherein the sensor comprises a Hall effect sensor.

9. An implantable pulse generator (IPG) system limiting undesired current flow comprising in combination:

(a) an IPG housing (b) a signal generator disposed in the housing that generates an electrical signal;

(c) at least one lead extending from the housing and in electrical communication with the signal generator, wherein the lead conveys the electrical signal to electrically sensitive tissue;

(d) current limiting componentry within the IPG case comprising at least one capacitive element electrically coupled to at least one lead;

(e) at least one impedance increasing element serially coupled between the capacitive element and an electrical ground, wherein the capacitive element together with the impedance increasing element provides an alternating current impedance path to the electrical around from a lead coupled to the capacitive element; and (f) a second switching device coupled between the capacitive element and the impedance increasing element.

10. The IPG system of claim 9, further comprising:

(g) a signal sensor for sensing an external signal, wherein the signal sensor is coupled to the second switching device and wherein the signal sensor enables the second switching device when the sensor senses that a level of the external signal is greater than an external signal threshold.

11. The IPG system of claim 10, wherein the sensor comprises a telemetry antenna.

12. The IPG system of claim 10, wherein the sensor comprises a coil/transformer.

13. The IPG system of claim 10, wherein the sensor comprises a lead voltage sensor.

14. The IPG system of claim 10, wherein the sensor comprises a lead current sensor.

15. The IPG system of claim 10, wherein the sensor comprises a sensor for sensing a magnetic field effect.

16. The IPG system of claim 10, wherein the sensor comprises a Hall effect sensor.

17. An implantable pulse generator (IPG) system limiting undesired current flow comprising in combination:

(a) an IPG housing (b) a signal generator disposed in the housing that generates an electrical signal;

(c) at least one lead extending from the housing and in electrical communication with the signal generator, wherein the lead conveys the electrical signal to electrically sensitive tissue;

(d) current limiting componentry within the IPG case comprising at least one capacitive element electrically coupled to at least one lead; and (e) at least one impedance increasing element serially coupled between the capacitive element and an electrical ground, wherein the capacitive element together with the impedance increasing element provides an alternating current impedance path to the electrical ground from a lead coupled to the capacitive element, and wherein the impedance increasing element is a capacitive element that reduces the capacitance and increases the impedance of each alternating current impedance path.

18. An implantable pulse generator (IPG) system limiting undesired current flow comprising in combination:

(a) an IPG housing (b) a signal generator disposed in the housing that generates an electrical signal;

(c) at least one lead extending from the housing and in electrical communication with the signal generator, wherein the lead conveys the electrical signal to electrically sensitive tissue;

(d) current limiting componentry within the IPG case comprising at least one capacitive element electrically coupled to at least one lead; and (e) at least one impedance increasing element serially coupled between the capacitive element and an electrical ground, wherein the capacitive element together with the impedance increasing element provides an alternating current impedance path to the electrical ground from a lead coupled to the capacitive element, and wherein the capacitive element is a feed through capacitor.

19. An implantable pulse generator (IPG) system limiting undesired current flow comprising in combination:

(a) an IPG housing (b) a signal generator disposed in the housing that generates an electrical signal;

(c) at least one lead extending from the housing and in electrical communication with the signal generator, wherein the lead conveys the electrical signal to electrically sensitive tissue;

(d) current limiting componentry within the IPG case comprising at least one capacitive element electrically coupled to at least one lead;

(e) at least one impedance increasing element serially coupled between the capacitive element and an electrical ground, wherein the capacitive element together with the impedance increasing element provides an alternating current impedance path to the electrical around from a lead coupled to the capacitive element; and (f) at least one alternating current blocking element, wherein the alternating current blocking element is coupled between the capacitive element and a distal end of the lead coupled to the capacitive element.

20. The IPG system of claim 19, wherein the alternating current blocking element comprises an inductive element.

21. The IPG system of claim 19, wherein the alternating current blocking element comprises a ferrite bead.

22. The IPG system of claim 19, wherein the alternating current blocking element comprises a resistor.

23. An implantable pulse generator (IPG) system limiting undesired current flow comprising in combination:
   (a) an IPG housing
   (b) a signal generator disposed in the housing that generates an electrical signal;
   (c) at least one lead extending from the housing and in electrical communication with the signal generator, wherein the lead conveys the electrical signal to electrically sensitive tissue;
   (d) current limiting componentry within the IPG case comprising at least one capacitive element electrically coupled to at least one lead;
   (e) at least one impedance increasing element serially coupled between the capacitive element and an electrical ground, wherein the capacitive element together with the impedance increasing element provides an alternating current impedance path to the electrical ground from a lead coupled to the capacitive element; and
   (f) at least one resistor, wherein the resistor is coupled between the capacitive element and a distal end of the lead coupled to the capacitive element.

24. An implantable medical device for application of an electrical signal to electrically sensitive tissue and capable of limiting undesired current flow, the medical device comprising in combination:
   (a) a housing;
   (b) a signal generator disposed in the housing that generates the electrical signal;
   (c) a plurality of leads extending from the housing and in electrical communication with the signal generator, wherein at least one lead of the plurality of leads applies the electrical signal to the electrically sensitive tissue;
   (d) a plurality of capacitive elements, wherein each capacitive element of the plurality of capacitive elements is associated with a lead of the plurality of leads;
   (e) an impedance increasing element serially coupled between each of the plurality of capacitive elements and an electrical ground, wherein each capacitive element together with the impedance increasing element provides an alternating current impedance path to the electrical ground from a lead coupled to the capacitive element;
   (f) a first switching device coupled between each capacitive element of the plurality of capacitive elements and the electrical ground;
   (g) a second switching device coupled between each capacitive element of the plurality of capacitive elements and the impedance increasing element; and
   (h) a signal sensor for sensing an external signal, wherein the signal sensor is coupled to each of the first switching device and the second switching device and wherein the signal sensor disables the first switching device and enables the second switching device when the sensor senses that a level of the external signal is greater than an external signal threshold.

* * * * *

UNITED STATES PATENT AND TRADEMARK OFFICE
CERTIFICATE OF CORRECTION

PATENT NO. : 6,901,292 B2  
DATED : May 31, 2005  
INVENTOR(S) : Hrdlicka et al.

It is certified that error appears in the above-identified patent and that said Letters Patent is hereby corrected as shown below:

Column 9,
Lines 7 and 44, "electrical around" should read -- electrical ground --.

Signed and Sealed this

Sixteenth Day of May, 2006

JON W. DUDAS  
*Director of the United States Patent and Trademark Office*

UNITED STATES PATENT AND TRADEMARK OFFICE
CERTIFICATE OF CORRECTION

| | | |
|---|---|---|
| PATENT NO. | : 6,901,292 B2 | Page 1 of 1 |
| APPLICATION NO. | : 10/034945 | |
| DATED | : May 31, 2005 | |
| INVENTOR(S) | : Hrdlicka et al. | |

It is certified that error appears in the above-identified patent and that said Letters Patent is hereby corrected as shown below:

Column 9, Line 7: "electrical around" should read --electrical ground-- ;

Column 9, Line 44: "electrical around" should read --electrical ground--.

Signed and Sealed this

Sixth Day of February, 2007

JON W. DUDAS
*Director of the United States Patent and Trademark Office*